(12) United States Patent
Krensky

(10) Patent No.: US 10,835,339 B2
(45) Date of Patent: Nov. 17, 2020

(54) SURGICAL INSTRUMENT AND ACCESSORY ORGANIZER

(71) Applicant: SEVILLE MEDICAL INC., Toronto (CA)

(72) Inventor: Robert Krensky, Toronto (CA)

(73) Assignee: SEVILLE MEDICAL INC., Toronto (CA)

( * ) Notice: Subject to any disclaimer, the term of this patent is extended or adjusted under 35 U.S.C. 154(b) by 196 days.

(21) Appl. No.: 16/018,656

(22) Filed: Jun. 26, 2018

(65) Prior Publication Data

US 2018/0368932 A1 Dec. 27, 2018

Related U.S. Application Data

(60) Provisional application No. 62/524,861, filed on Jun. 26, 2017.

(51) Int. Cl.
*A61B 50/33* (2016.01)
*A61B 50/30* (2016.01)
*A61B 50/20* (2016.01)

(52) U.S. Cl.
CPC .............. *A61B 50/33* (2016.02); *A61B 50/20* (2016.02); *A61B 50/3001* (2016.02); *A61B 2050/3008* (2016.02); *A61B 2050/3011* (2016.02)

(58) Field of Classification Search
CPC ..... A61B 50/33; A61B 50/20; A61B 50/3001; A61B 2050/3008; A61B 2050/3011; A61L 2/07; A61L 2/26; A61L 2202/182

USPC .............................. 206/370, 477; 211/85.13
See application file for complete search history.

(56) References Cited

U.S. PATENT DOCUMENTS

| | | | | | |
|---|---|---|---|---|---|
| 2,018,651 | A | * | 10/1935 | Bates | A61C 19/02 206/370 |
| 4,323,062 | A | * | 4/1982 | Canty | A61M 25/02 128/852 |
| 5,492,671 | A | * | 2/1996 | Krafft | A61L 2/06 422/26 |
| 5,681,539 | A | * | 10/1997 | Riley | A61L 2/26 206/370 |
| 5,725,097 | A | * | 3/1998 | Bettenhausen | A61C 19/02 206/1.5 |
| 5,827,487 | A | * | 10/1998 | Holmes | A61L 2/26 422/297 |
| 5,843,387 | A | * | 12/1998 | Dane | A61L 2/26 422/300 |
| 5,913,422 | A | * | 6/1999 | Cote | A61L 2/26 206/210 |
| 6,012,577 | A | * | 1/2000 | Lewis | A61L 2/26 206/370 |
| 6,193,932 | B1 | * | 2/2001 | Wu | A61L 2/07 206/210 |

(Continued)

*Primary Examiner* — Chun Hoi Cheung
(74) *Attorney, Agent, or Firm* — Aird & McBurney LP

(57) ABSTRACT

A surgical instrument and accessory organizer comprising a base pad having a lower surface and an upper surface and, the upper surface comprising at least one section for retaining instruments having a flat portion; at least one section for retaining instruments with a handle; at least one section for retaining fluids; and a plurality of perforations extending from the lower surface to the upper surface for removably attaching at least one retaining member adapted to maintain at least one of an instrument and an object in place.

18 Claims, 6 Drawing Sheets

(56) References Cited

U.S. PATENT DOCUMENTS

| | | | | |
|---|---|---|---|---|
| 6,244,447 B1 * | 6/2001 | Frieze | A61L 2/07 | 206/370 |
| 6,331,280 B1 * | 12/2001 | Wood | A61L 2/26 | 206/268 |
| 6,426,041 B1 * | 7/2002 | Smith | A61L 2/26 | 206/223 |
| 6,579,503 B1 * | 6/2003 | Tanamal | A61L 2/26 | 206/370 |
| 6,713,029 B1 * | 3/2004 | Krafft | A61L 2/07 | 206/370 |
| 6,969,498 B1 * | 11/2005 | Riley | A61L 2/26 | 206/363 |
| 8,069,998 B2 * | 12/2011 | Thomas | A61L 2/26 | 211/85.13 |
| 8,177,064 B2 * | 5/2012 | McCormick | A61B 50/33 | 206/370 |
| 8,272,508 B2 * | 9/2012 | Bettenhausen | A61L 2/26 | 206/370 |
| 8,915,363 B2 * | 12/2014 | Hawkes | A61C 19/002 | 206/366 |
| 10,039,897 B2 * | 8/2018 | Norris | A61M 25/002 | |
| 10,456,210 B2 * | 10/2019 | Jung | A61B 50/20 | |
| 10,575,933 B2 * | 3/2020 | Berg | A61B 50/30 | |
| 2006/0272979 A1 * | 12/2006 | Lubbers | A61B 50/20 | 206/557 |
| 2007/0205123 A1 * | 9/2007 | Bettenhausen | A61B 50/20 | 206/363 |
| 2009/0146032 A1 * | 6/2009 | Bettenhausen | A61B 50/30 | 248/220.31 |
| 2010/0174415 A1 * | 7/2010 | Humayun | A61F 9/00736 | 700/282 |
| 2011/0155599 A1 * | 6/2011 | Yakel | A61B 50/362 | 206/365 |
| 2014/0083886 A1 * | 3/2014 | Winterrowd | A61B 50/34 | 206/370 |
| 2015/0151017 A1 * | 6/2015 | Tipton | A61B 50/30 | 422/310 |
| 2019/0060022 A1 * | 2/2019 | Jung | A61B 50/20 | |

* cited by examiner

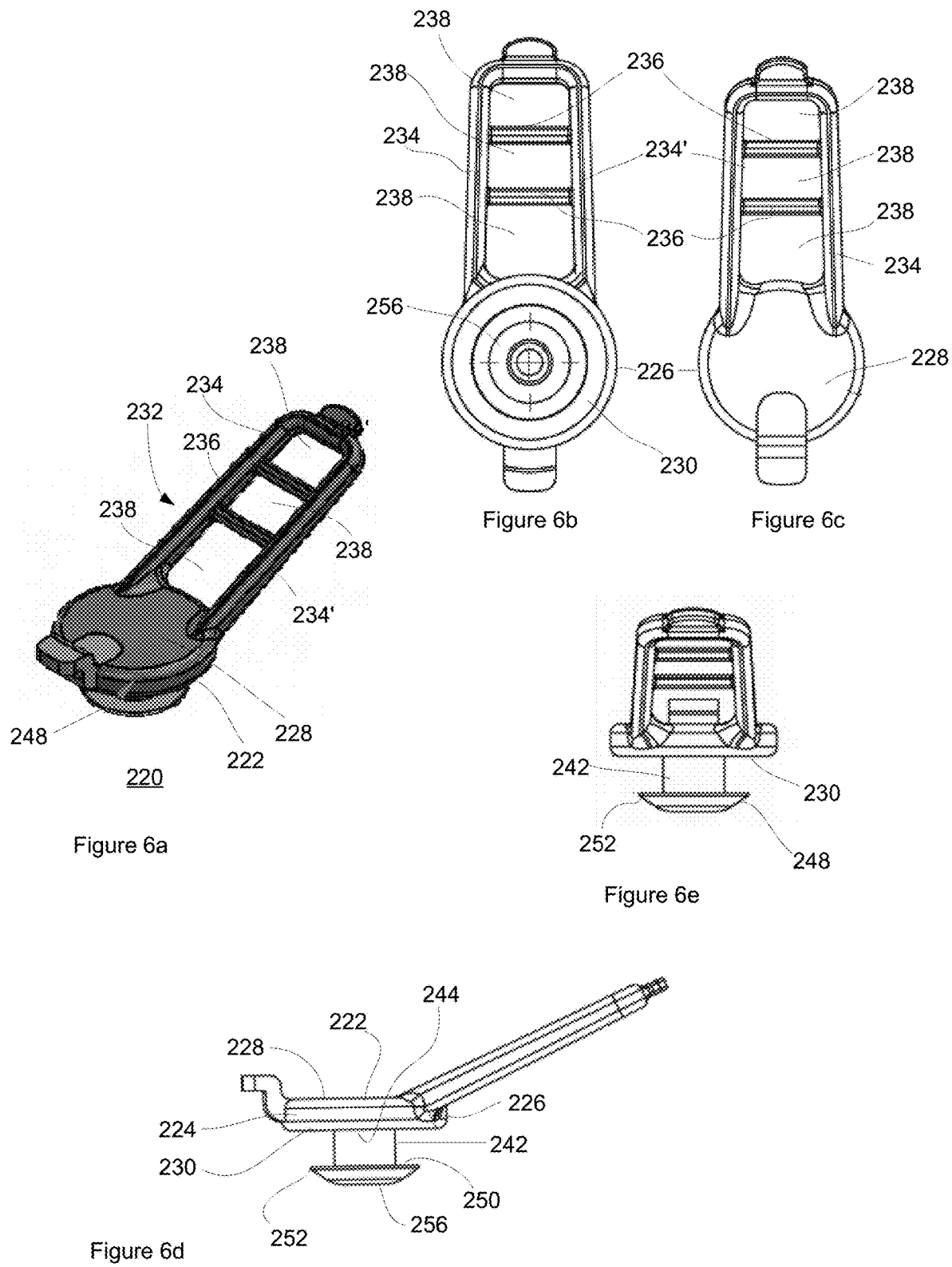

SURGICAL INSTRUMENT AND ACCESSORY ORGANIZER

CROSS-REFERENCE TO RELATED APPLICATIONS

This application claims the benefit of U.S. Provisional Patent Application No. 62/524,861, filed on Jun. 26, 2017.

FIELD OF THE INVENTION

The present invention relates to organizing medical instruments and accessories during a surgical procedure.

BACKGROUND

In the United States alone there are over 50 million surgical procedures annually. These surgical procedures typically involve the use of a variety of instruments and accessories, which are placed on an elevated sterile table top adjacent to the operating table. For easier access by the surgeon, often-times the instruments and accessories are placed directly on the surgical drape covering the patient. The instruments may include scalpels, scissors, forceps and electrocautery pens among others. When placed on the drape, even if a folded surgical towel or other improvised method is used to provide an underlying support or "work area" for the instruments and accessories, these instruments and accessories may still become mobile due to the irregular contours of the patient, and are prone to rolling off the drape. Any instruments that roll off the sterile field are required to be discarded and replaced if single-use (disposable) or re-sterilized (reusable) before they can be used again. Reusable instruments may also be damaged which would require repair or permanent replacement. Replacement of surgical instruments during surgery, especially when the loss from the table has gone unnoticed, can lead to frustration for the surgical staff. For the surgical facility, intraoperative instrument replacement leads to wasted resources and unnecessary replacement costs. In addition, should instruments with pointed ends or sharp ends, such as syringes and surgical scalpels, roll off then they may present an occupational health hazard to the medical personnel if any one of them is scratched, or receives a skin puncture, by the needle point, blade point or other pointed end of a sharp surgical instrument. Other items, such as vacuum suction and cardiopulmonary bypass tubing, must be secured in some fashion to the surgical draping using various holders and drape clamps.

One commercially available approach for securing surgical instruments is a reusable magnetic pad that is placed onto the surgical drape such that metal instruments stick to the pad and remain in fixed positions. However, magnetic pads may interfere with implanted medical devices, such as pacemakers. Also, metal instruments can become magnetized which can then make the picking up of fine metal products such as suture needles troublesome and frustrating. Another drawback is that plastic or other non-metal surgical materials or products cannot be used with magnetic pads.

Another approach includes quiver-like products that are provided as part of a surgical electrocautery pack. However, these quiver-like products are generally difficult to adequately secure and may loosen or rotate during the surgery thereby allowing the instruments contained within to fall out onto the floor.

Yet another approach involves the use of VELCRO®-type ties that are integrated into disposable surgical drapes at various fixed locations determined by the drape manufacturer. However, this approach can be problematic because these straps are not always located in the most convenient location. With over 50 million surgical cases performed in the U.S. alone each year, a solution to the above-noted problems is very much desired.

It is an object of the present invention to mitigate or obviate at least one of the above-mentioned disadvantages.

SUMMARY OF THE INVENTION

In one of its aspects, there is provided a base pad comprising a lower surface and an upper surface, the base pad comprising:
a first base pad portion and a second base pad portion, and an intermediate portion between the first base pad portion and the second base pad portion;
a plurality of perforations extending from the lower surface to the upper surface, the plurality of perforations formed in a section of the first base pad portion and a second base pad portion; the plurality of perforations for removably attaching at least one retaining member adapted to maintain at least one of an instrument and an object in place;
at least one periphery of the first base pad portion and the second base pad portion, the at least one periphery having a longitudinal raised wall with raised walls on either side of the longitudinal raised wall to define a pocket;
at least one resilient loop integrally formed with at least one of the first base pad portion and the second base pad, the at least one resilient loop having an opening defined therethrough for receiving the at least one of an instrument and an object;
formed with the intermediate portion, a first series of upstanding walls separated from each other by a first channel, the first channel being dimensioned to receive a first shank of the at least one of an instrument and an object; and a second series of upstanding walls separated from each other by a second channel, the second channel being dimensioned to receive a second shank of the at least one of an instrument and an object having at least one of a needle point, blade point or other pointed end, and a third series of upstanding walls separated from each other by a slit, the slit disposed collinearly with the second channel to receive the at least one of a needle point, blade point or other pointed end of the at least one instrument and an object.

In another of its aspects, there is provided a surgical instrument and accessory organizer comprising:
a base pad having a lower surface and an upper surface and, the upper surface comprising:
    at least one section for retaining instruments having a flat portion; at least one section for retaining instruments with a handle;
    at least one section for retaining fluids; and
    a plurality of perforations extending from the lower surface to the upper surface for removably attaching at least one retaining member adapted to maintain at least one of an instrument and an object in place.

In another of its aspects, there is provided a kit comprising:
a base pad having an upper section and a lower surface and an upper section, the based pad comprising a plurality of perforations extending from the lower surface to the upper surface for removably attaching a plurality of accessories adapted to maintain at least one of an instrument and an object in place; a periphery with at least one portion having a longitudinal raised wall with raised walls on either side of the longitudinal raised wall to define a pocket; at least one resilient loop integrally formed therewith, the at least one resilient loop having an opening defined therethrough for receiving the at least one of an instrument and an object; a first series of upstanding walls separated from each other by a channel, the channel being dimensioned to receive a shank of the at least one of an instrument and an object and a second series of upstanding walls separated from each other by a slit, the slit disposed collinearly with the first channel to receive a portion of the at least one of an instrument and an object having at least one of a needle point, blade point or other pointed end; and at least one retaining member for retaining at least one of the instrument and the object, wherein the at least one retaining member comprises a structure suitable to retain the at least one of the instrument and the accessory, the structure comprising at least one disc integrally formed therewith, the at least one disc having a top surface coupled to the structure and a bottom surface with a peg extending from the bottom surface at one end of the peg and a frustoconical cap at another end of the peg, frustoconical cap comprising a peripheral edge, wherein the frustoconical cap is insertable into the perforations by introducing the peripheral edge into the perforation and pushing the peg through the perforation such that the frustoconical cap abuts the lower surface of the base pad.

In another of its aspects, there is provided a method for maintaining at least one of an instrument and an object in place during a procedure, the method comprising the steps of:

draping a surgical instrument and accessory organizer on a patient adjacent a site of the procedure on the patient, the surgical instrument and accessory organizer comprising a base pad having a lower surface and an upper surface;

inserting at least one of an instrument and an object in an opening defined of at least one resilient loop integrally formed the base pad;

placing at least one of a first shank of the at least one of the instrument and the object in one of first channel defined in a first series of upstanding walls and a second shank of the at least one of the instrument having at least one of a needle point, blade point or other pointed end in a second channel defined within a second series of upstanding walls and placing the at least one of a needle point, blade point or other pointed end in a slit defined in a third series of upstanding walls, the slit disposed collinearly with the second channel;

removably attaching at least one retaining member in at least one perforation formed in the base pad, the at least one retaining member comprising a structure suitable to retain the at least one of the instrument and the object; and maintaining the at least one instrument or the object or fluid in at least one pocket defined within at least one periphery of the base pad.

Advantageously, the surgical instrument and accessory organizer apparatus improves the organization of instruments and accessories during surgical procedures, thereby minimizing replacement costs and damage resulting from unsecured instruments from dropping on to the floor. Furthermore, sharp instruments may be held securely in place thus minimizing exposure to sharps, such as needles, scalpels and other medical procedure objects, devices or instruments, to medical personnel, thereby reducing the risk of injuries. Pathogenic microorganisms may be present in human blood, body fluids or other infected materials and may cause infection and disease in persons who are percutaneously, or mucocutaneously, exposed, and so such risk to infection and disease is also reduced. In addition, setting out the medical instruments and accessories neatly on the organizer allows for quick and easy access and accountability for all medical instruments and accessories during the surgical procedure. The occupational health risk is also mitigated by the use of the surgical instrument area as a safe transfer zone of sharp instruments between the surgeon and scrub nurse as opposed to a direct hand-to-hand transfer.

BRIEF DESCRIPTION OF THE DRAWINGS

Several exemplary embodiments of the present invention will now be described, by way of example only, with reference to the appended drawings in which:

FIG. 3b shows an exploded view of the exemplary accessory of FIG. 3a;

FIGS. 6a, 6b, 6c, 6d and 6e show views of an exemplary tubing holder;

DETAILED DESCRIPTION OF EXEMPLARY EMBODIMENTS

The detailed description of exemplary embodiments of the invention herein makes reference to the accompanying block diagrams and schematic diagrams, which show the exemplary embodiment by way of illustration. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented.

Figure 1:
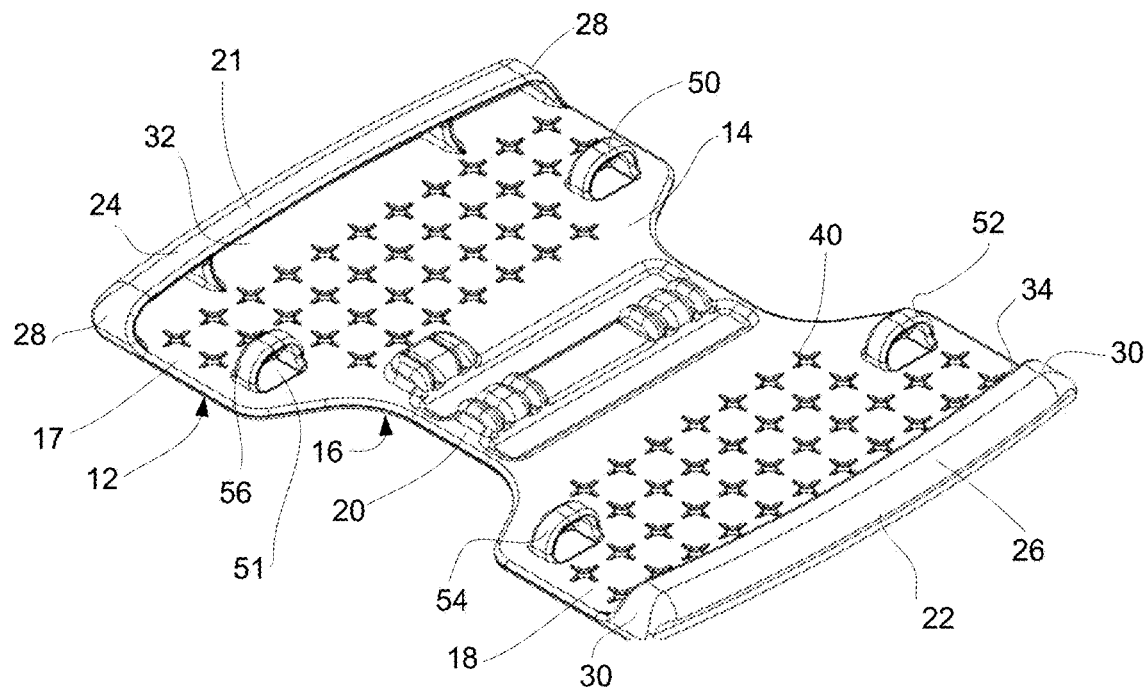
FIG. 1 shows a front perspective view of a surgical instrument and accessory organizing apparatus, in one embodiment.

FIG. 1 shows an exemplary surgical instrument and accessory organizer, generally identified by reference numeral 10, comprising body 12 with a top surface 14 and bottom surface 16. Body 12 is a flexible, planar base pad with opposed portions 17, 18, separated by intermediate portion 20. Each of opposed portions 17, 18 includes opposed lateral sides 21, 22, having raised longitudinal walls 24, 26 and side walls 28, 30 defining pockets 32, 34, respectively. Pockets 32, 34 retain fluids or instruments or accessories. Pockets 32, 34 may include dividing walls to define additional compartments therewithin. Opposed portions 17, 18 further include a plurality of perforations 40 in a grid pattern dimensioned for removable attachment of accessories adapted to retain instruments and other accessories or objects. During a surgical procedure surgical instrument and accessory organizer 10 is placed adjacent to the surgical site, such as on a patient chest, abdomen or legs, and conforms to the contours of the patient's body due to its flexibility and drapability. Generally, surgical instrument and accessory organizer 10 is hour glass-shaped to allow for access to certain areas of the patient such as the groin and to provide adequate space for surgical instruments, such as a surgical wound retractor.

Integrally-formed in opposed portions 17, 18, are resilient loops 50, 52, 54 and 56 for retaining instruments and accessories, such as cautery pens, and handheld medical instruments, via openings 51. Resilient loops 50, 52, 54 and 56 may include a range of differently dimensioned openings 51 to accommodate a range of differently dimensioned instruments and accessories.

Figure 2:
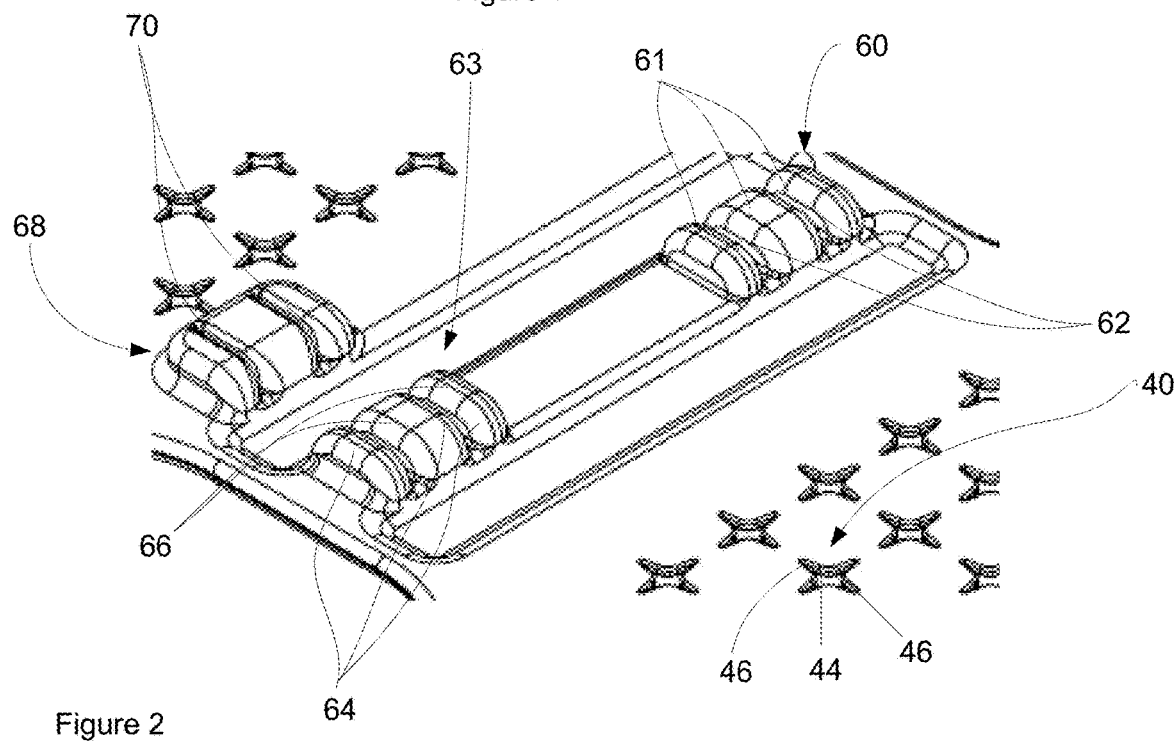
FIG. 2 shows an exploded front perspective view of the surgical instrument and accessory organizing and holding apparatus.

As shown in FIG. 2, intermediate portion 20 comprises integrally-formed resilient raised portion 60 with a series of upstanding walls 61 separated from each other by channels 62, such that channels 62 are dimensioned to receive a variety of instruments or accessories. Channels 62 longitudinally extend substantially the full length of raised portion 60. In one implementation, an instrument having at least a longitudinal shank portion is placed within channel 62, and the shank portion is held in place by opposed resilient, upstanding walls 61 pushing against the shank portion. Also disposed within intermediate portion 20 is another integrally-formed resilient raised portion 63 with a series of integrally-formed resilient, upstanding walls 64 separated from each other by channels 66. Channels 66 longitudinally extend substantially the full length of raised portion 63. Positioned adjacent to a series of integrally-formed resilient, upstanding walls 64 is raised portion 68 with slits 70 co-linear with channels 66. Accordingly, in one implementation, instruments with a needle point, blade point or other pointed end may be secured on the surgical instrument and accessory organizer 10 within slits 70 and channels 66. For example, a scalpel having a shank portion and a blade is secured on surgical instrument and accessory organizer 10 by placing the shank portion within channel 66, and by placing the sharp blade within slit 70. Therefore, the shank portion of the scalpel is held in place by opposed resilient, upstanding walls 61 pushing against the shank portion, and the sharp blade is safely contained within slit 70 which minimizes accidental cuts, punctures, scratches, or nicks to medical personnel, or accidental damage to medical equipment and accessories. Opposed resilient, upstanding walls 61, 64 may include various heights to accommodate a range of differently dimensioned instruments and accessories, and channels 64, 66, and slits 70 also may include various heights, lengths, widths and shapes to accommodate a range of differently dimensioned instruments and accessories. Raised portion 63 and raised portion 68 are appropriately spaced to facilitate grasping of an instrument or object for both placement within slits 70 and/or channels 66, including removal therefrom.

Figure 3A:
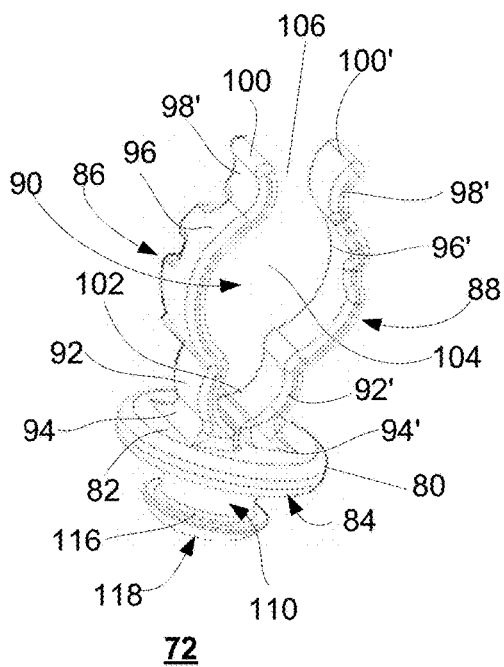
FIG. 3a shows a perspective view of an exemplary accessory.
Figure 3B:
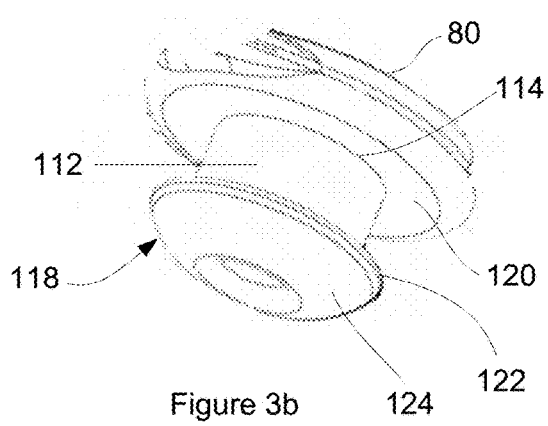

FIGS. 3*a* and 3*b* show exemplary accessory clip member 72 which comprises a disc 80 with top surface 82 and bottom surface 84, and integrally formed with disc 80 is a pair of resilient arms 86, 88 projecting from top surface 82. Arms 86, 88 comprises similar halves disposed opposite each other, with a spacing 90 defined therebetween for receiving at least one surgical tubing. Each arm 86, 88 comprises bottom arcuate portion 92, 92' with one end 94, 94' formed with top surface 82, adjacent to the center of disc 80, and middle arcuate portion 96, 96' coupled to arcuate portion 92, 92', and top arcuate portion 98, 98' with guide lip 100, 100' diverging outwardly away from middle arcuate portion 96, 96'. Spacing 90 comprises spacing 102 defined between bottom arcuate portions 92 and 92', spacing 104 defined between middle arcuate portions 96, and spacing 106 defined between top arcuate portion 98, 98'. Accordingly, an instrument or accessory is introduced into clip member 72 via guide lips 100, 100' into spacing 106. Depending on the circumferential girth of the tubing arcuate portions 96 and 96' may be caused to separate from each other to accommodate different sizes of tubing. Accordingly, the tubing may be dimensioned to come to rest within spacing 104 or within spacing 102, depending on the dimensions thereof. Arms 86, 88 may be formed from a material that has sufficient elasticity or resiliency so that corresponding arms 86, 88 can be spread apart or deformed during insertion and removal of the tubing laterally through the spacing 90, between the arms 86, 88.

Integrally formed with disc 80 and extending from bottom surface 84 is peg 110 with cylindrical peg body 112. One end 114 of peg body 112 is integrally formed with bottom surface 84 and other end 116 of peg body 112 comprises frustoconical cap 118 having undersurface 120 with peripheral edge 122, with frustoconical cap body 124 extending uniformly inwardly from peripheral edge 122 to top surface 126.

Figure 3C:
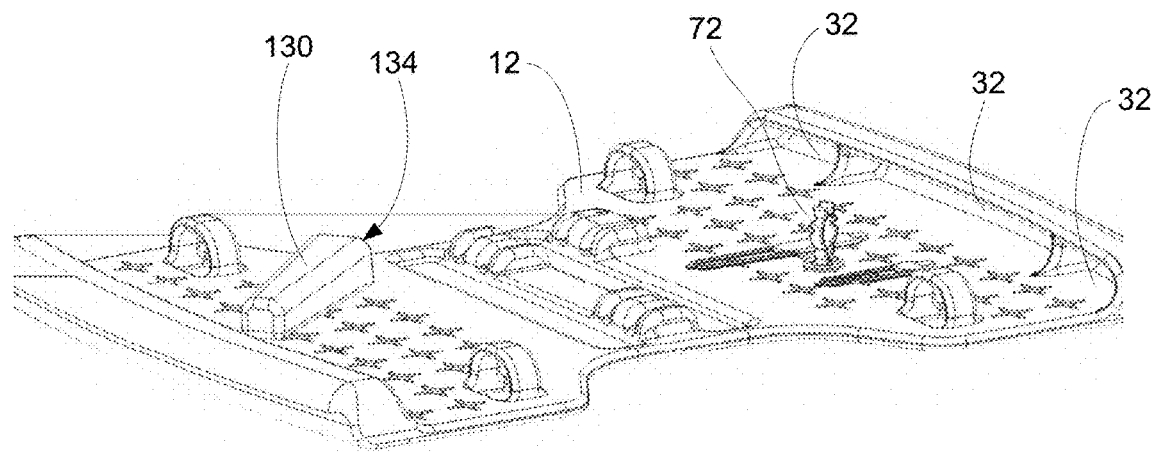
FIG. 3c shows a perspective view of the apparatus of FIG. 1 with a plurality of accessories secured thereon.

In operation, clip member 72 is removably attached to one of the plurality of perforations 40 of body 12. As shown in FIG. 3*c*, frustoconical cap 118 is inserted into star perforation 40 by introducing peripheral edge 122 in central opening 44 and opposing slits 46, and pushing peg body 112 through central opening such that frustoconical cap body 124 abuts bottom surface of body 12 and bottom surface 84 of disc 80 abuts top surface of body 12. The body 12 is formed from a material that has sufficient elasticity or resiliency so that opposing slits 46 can be urged apart or deformed during insertion and removal of frustoconical cap 118. As such, tubing is securely attached on body 112 and peg body 112 has freedom of movement within central opening 44 to allow for rotation of the tubing to facilitate placing the tubing in a desired orientation in a particular application.

Looking at FIG. 3*c*, another accessory is instrument housing 130 having a quiver-like shell body 132 with longitudinal cavity 134 defined therein for receiving and retaining instruments or objects, such as cautery pens. Longitudinal cavity 134 may be of sufficient depth and configuration to retain a variety of instruments or the proximal ends or handles of the instruments being presented for grasping. Body 132 comprises integrally formed longitudinal walls 135 with opening 138 at one end 140 and base 142 at another end 144. Opening 138 provides access for insertion and removal of instruments or accessories. Formed with shell body 132 is disc 150, similar to disc 80, and extending from bottom surface 152 of disc 150 is peg 154 with cylindrical peg body 156. One end 158 of peg body 112 is integrally formed with bottom surface 152 and other end 160 of peg body 156 comprises frustoconical cap 162 having undersurface 164 with peripheral edge 166, with frustoconical cap body 168 extending uniformly inwardly from peripheral edge 166 to top surface 170.

Figure 4A:
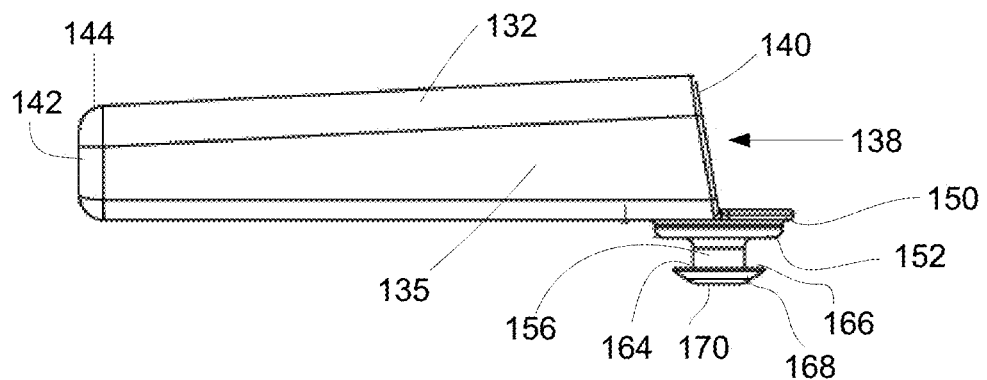
FIGS. 4a, 4b, and 4c show views of an exemplary instrument holder.
Figure 4B:
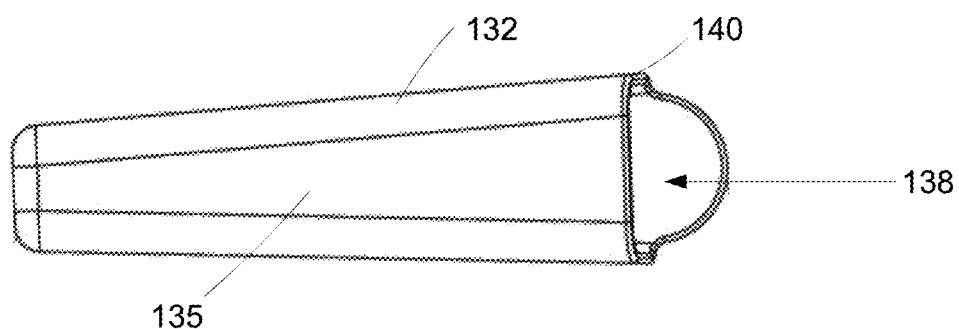
Figure 4C:
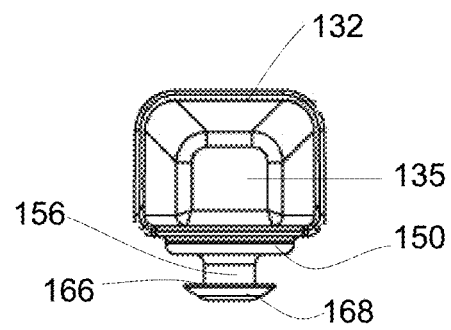
Figure 5A:
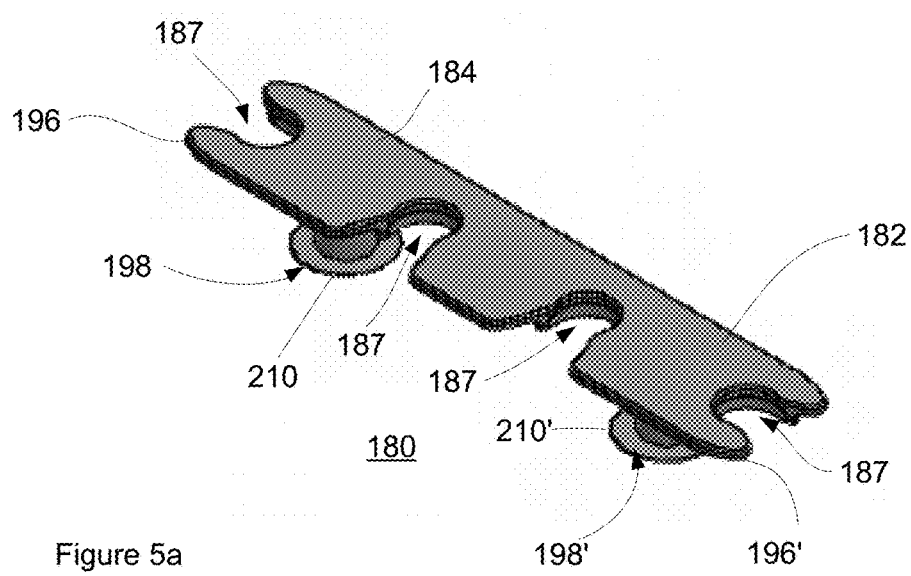
FIGS. 5a, 5b, 5c, and 5d show views of an exemplary base plate for tubing clamp rack.
Figure 5B:
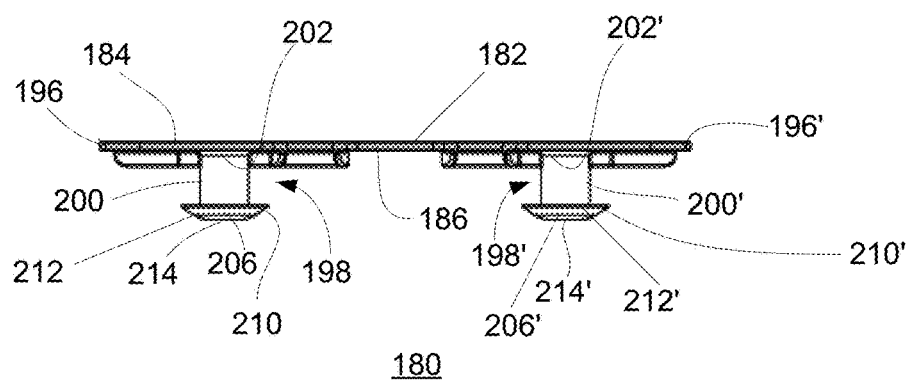
Figure 5C:
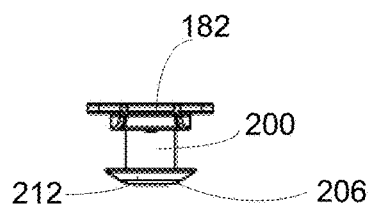
Figure 5D:
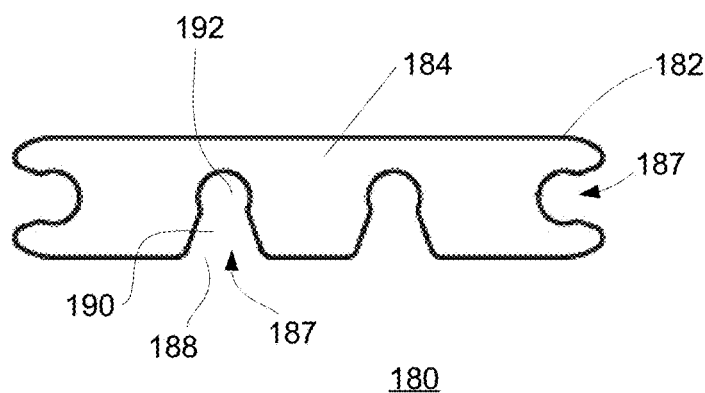

In operation, instrument housing 130 is removably attached to one of the plurality of perforations 40 of body 12. As shown in FIGS. 4*a*, 4*b* and 4*c*, frustoconical cap 162 is inserted into star perforation 40 by introducing peripheral edge 166 in central opening 44 and opposing slits 46, and pushing peg body 112 through central opening such that frustoconical cap body 168 abuts bottom surface of body 12 and bottom surface 84 of disc 80 abuts top surface of body 12. As such, instrument housing 130 is securely attached on body 12 with one of integrally formed longitudinal walls 135 also abutting or adjacent to top surface of body 12. Peg body 156 has freedom of movement within central opening 44 to allow for rotation of instrument housing 130 to facilitate use in certain applications, or desired placement.

Now turning to FIGS. 5a, 5b, 5c, and 5d, another exemplary accessory is tubing clamp rack 180 having a plate body 182 with upper surface 184 and lower surface 186, with slots 187 in plate body 182 for receiving single tubing clamps 220. Slots 187 comprise mouth opening 188 with narrowing entrance slot 190 to rounded slot portion 192. Generally, opposed ends 196, 196', include pegs 198, 198', with cylindrical peg body 200, 200', respectively. Each end 202, 202' of peg body 200, 200' is integrally formed with lower surface 186 and other end 204, 204' of peg body 200, 200' comprises frustoconical cap 206, 206' having undersurface 208, 208' with peripheral edge 210, 210', with frustoconical cap body 212, 212' extending uniformly inwardly from peripheral edge 210, 210' to top surface 214, 214. In other implementations, clamp rack 180 may comprise additional or fewer slots 187, as desired.

Figure 7:
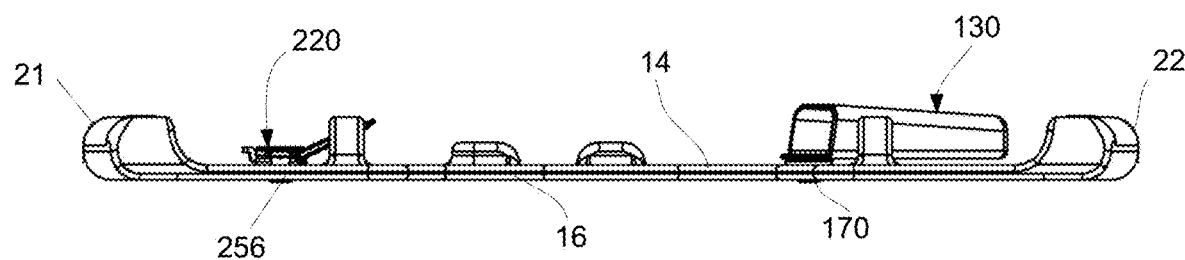
FIG. 7 shows a side view of the apparatus of FIG. 1 with a plurality of accessories secured thereon.
Figure 8:
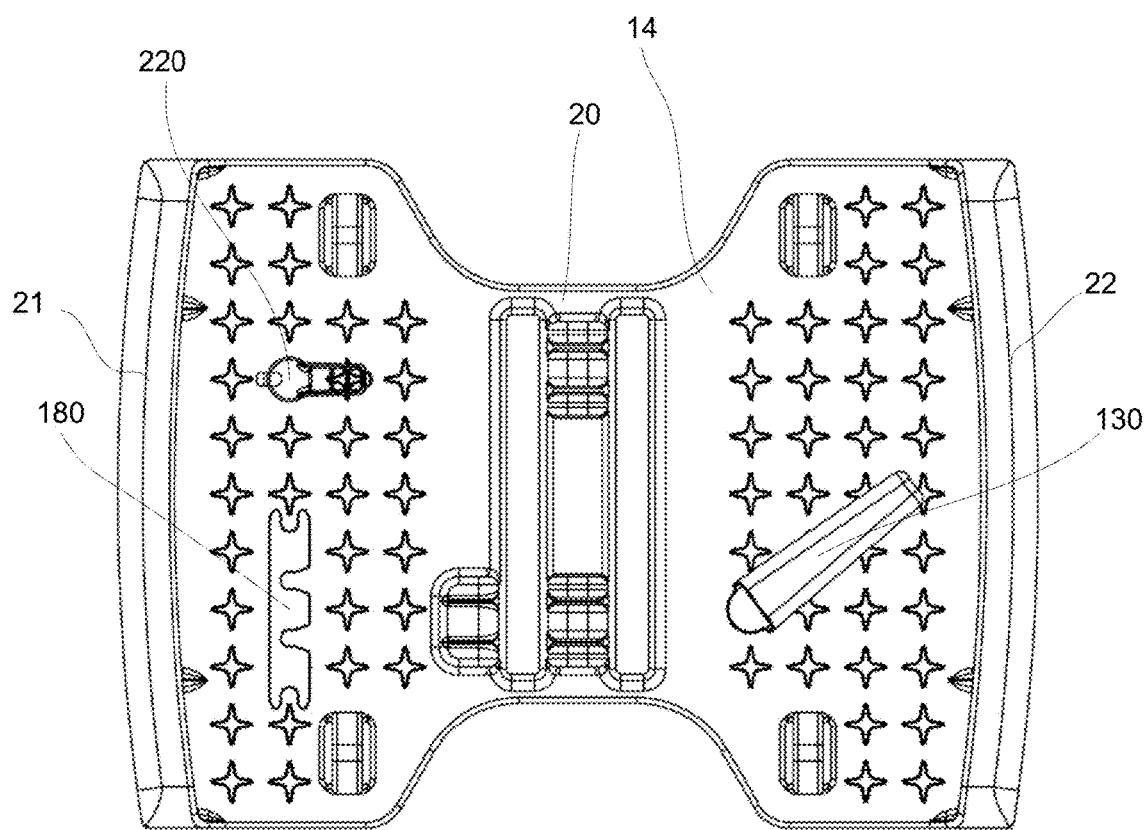
FIG. 8 shows a perspective view of the apparatus of FIG. 1 with a plurality of accessories secured thereon.

In operation, tubing clamp rack 180 is removably attached to two of the plurality of perforations 40 of body 12. As shown in FIGS. 7 and 8, frustoconical caps 206, 206' are inserted into star perforations 40 by introducing peripheral edges 210, 210' in central opening 44 and opposing slits 46, and pushing peg body 200, 200' through central opening 44 such that frustoconical cap body 212, 212' abuts bottom surface of body 12 and lower surface 186 of plate body 182 abuts top surface of body 12. As such, clamp rack 180 is securely attached on body 12 by cylindrical peg body 200, 200'.

FIGS. 6a, 6b, 6c, 6d and 6e show hose clamp 220 which comprises disc 222 having disc body 224 with peripheral edge 226, top surface 228 with catch member 229, and bottom surface 230. Extending from disc body 224 and adjacent to peripheral edge 226 is ladder-like member 232 comprising angled, flexible and elongate members 234, 234' with bottom rung member 236a, intermediate rung member 236b, and top rung member 236c there between. Spacings 238 are defined between elongate members 234, 234' and rung members 236. In operation, tubing is placed on top surface 226, and ladder-like member 232 is bent forward such that one of rung members 236a, 236b or 236c engages catch member 229 thereby securing the tubing between flexible and elongate members 234, 234' and top surface 228. Accordingly, one of rung members 236a, 236b or 236c is selected for engagement with catch member 229 depending on the dimension of the tubing. Top rung member 236c comprises tab 237 to facilitate engagement and disengagement of rung members 236a, 236b, 236c from catch member 229. Extending from bottom surface 230 is peg 240 with cylindrical peg body 242. One end 244 of peg body 242 is integrally formed with bottom surface 230 and other end 246 of peg body 242 comprises frustoconical cap 248 having undersurface 250 with peripheral edge 252, with frustoconical cap body 254 extending uniformly inwardly from peripheral edge 252 to top surface 256.

Accordingly, cylindrical peg body 242 of hose clamp 220 is introduced into slot 187 of clamp rack 180, either directly into rounded slot portion 192, or via mouth opening 188 into converging entrance slot 190 to rest in rounded slot portion 192. Peg body 242 has freedom of movement within rounded slot portion 192 to allow for rotation of hose clamp 220 to facilitate use in certain applications, or desired placement. Alternatively, frustoconical cap 248 is inserted directly into body 12 via star perforations 40 by introducing peripheral edge 226 in central opening 44 and opposing slits 46, and pushing peg body 242 through central opening 44 such that frustoconical cap body 254 abuts bottom surface of body 12 and undersurface 250 of frustoconical cap 248 abuts lower surface 16 of body 12. As such, hose clamp 220 is securely attached on body 12 by cylindrical peg body 242 and peg body 1242 has freedom of movement within central opening 44 to allow for rotation of hose clamp 220 to facilitate use in certain applications.

Perforations 40 may be differently-sized to accommodate a range of differently dimensioned accessories.

In another exemplary implementation, intermediate portion 20 of body 12 is substantially non-flexible, while opposed portions 17, 18 are flexible.

In another exemplary implementation, intermediate portion 20 of body 12 is disposed elsewhere on body 12.

In another exemplary implementation, opposed portions 17, 18 and intermediate portion comprise raised walls, such that body 12 comprises a raised perimeter wall along its peripheral edges, to substantially contain fluids, and maintain instruments and accessories on top surface 14.

In another exemplary implementation, the surgical instrument and accessory organizer is made from silicone rubber, or other suitable material that is sterilizable.

In another exemplary implementation, the surgical instrument and accessory organizer and the accessories may be disposable or reusable by following re-sterilization.

In another exemplary implementation, any of discs 80, 150, 222 associated with the accessories mentioned above comprise a Velcro type hook or loop fastener for removable attachment to surgical instrument and accessory organizer 10. For example, a loop side Velcro fastener is adhesively adhered to the underside of discs 80, 150, 222 and top portion 14 of surgical instrument and accessory organizer 10 comprises a hook side Velcro fastener, or vice versa.

While these exemplary embodiments are described in sufficient detail to enable those skilled in the art to practice the invention, it should be understood that other embodiments may be realized and that logical and mechanical changes may be made without departing from the spirit and scope of the invention. The preceding detailed description is presented for purposes of illustration only and not of limitation, and the scope of the invention is defined by the preceding description, and with respect to the attached claims.

The invention claimed is:

1. A base pad comprising a lower surface and an upper surface, the base pad comprising:
   a first base pad portion and a second base pad portion, and an intermediate portion between the first base pad portion and the second base pad portion;
   a plurality of perforations extending from the lower surface to the upper surface, the plurality of perforations formed in a section of the first base pad portion and a second base pad portion; the plurality of perforations for removably attaching at least one retaining member adapted to maintain at least one of an instrument and an object in place;
   at least one periphery of the first base pad portion and the second base pad portion, the at least one periphery having a longitudinal raised wall with raised walls on either side of the longitudinal raised wall to define a pocket;
   at least one resilient loop integrally formed with at least one of the first base pad portion and the second base pad, the at least one resilient loop having an opening defined therethrough for receiving the at least one of an instrument and an object; and formed with the intermediate portion, a first series of upstanding walls separated from each other by a first channel, the first channel being dimensioned to receive a first shank of the at least one of an instrument and an object; and a second series of upstanding walls separated from each other by a second channel, the second channel being dimensioned to receive a second shank of the at least one of an instrument and an object having at least one of a needle point, blade point or other pointed end, and a third series of upstanding walls separated from each other by a slit, the slit disposed collinearly with the second channel to receive the at least one of a needle point, blade point or other pointed end of the at least one of an instrument and an object.

2. The base pad of claim 1, wherein the first base pad portion and the second base portion are flexible, such that the base pad is drapable.

3. The base pad of claim 2, wherein the intermediate portion in rigid.

4. The base pad of claim 1, wherein the longitudinal raised wall comprises at least one dividing wall between the raised walls to divide the pocket into at least two compartments.

5. The based pad of claim 1, wherein the at least one retaining member comprises a structure suitable to retain the at least one of an instrument and an object, the structure comprising at least one disc integrally formed therewith, the at least one disc having a top surface coupled to the structure and a bottom surface with a peg extending from the bottom surface at one end of the peg and a frustoconical cap at another end of the peg, frustoconical cap comprising a peripheral edge, wherein the frustoconical cap is insertable into the perforations by introducing the peripheral edge into the perforation and pushing the peg through the perforation such that the frustoconical cap abuts the lower surface of the base pad.

6. A surgical instrument and accessory organizer comprising:
    a base pad having a lower surface and an upper surface and, the upper surface comprising:
        at least one section for retaining least one of an instrument and an object having a flat portion; at least one section for retaining instruments with a handle;
        at least one section for retaining fluids; and
        a plurality of perforations extending from the lower surface to the upper surface for removably attaching at least one retaining member adapted to maintain the at least one of an instrument and an object in place; and
    wherein the base pad comprises a periphery with at least one portion having a longitudinal raised wall with raised walls on either side of the longitudinal raised wall and opposed lateral side wall to define a pocket.

7. The surgical instrument and accessory organizer of claim 6, wherein the base pad comprises a resilient loop integrally formed therewith, the resilient loop having an opening defined therethrough for receiving the at least one of an instrument and an object.

8. The surgical instrument and accessory organizer of claim 6, wherein the base pad comprises a first series of upstanding walls separated from each other by a first channel, the first channel being dimensioned to receive a first shank of the at least one of an instrument and an object.

9. The surgical instrument and accessory organizer of claim 6, wherein the base pad comprises a second series of upstanding walls separated from each other by a second channel, the second channel being dimensioned to receive a second shank of the at least one of an instrument and an object having at least one of a needle point, blade point or other pointed end, and a third series of upstanding walls separated from each other by a slit, the slit disposed collinearly with the second channel and receiving the at least one of a needle point, blade point or other pointed end.

10. The surgical instrument and accessory organizer of claim 6, wherein the least one retaining member comprises a structure suitable to retain the at least one of the instrument and the accessory, the structure comprising at least one disc integrally formed therewith, the at least one disc having a top surface coupled to the structure and a bottom surface with a peg extending from the bottom surface at one end of the peg and a frustoconical cap at another end of the peg, frustoconical cap comprising a peripheral edge.

11. The surgical instrument and accessory organizer of claim 10, wherein the frustoconical cap is insertable into the perforations by introducing the peripheral edge into the perforation and pushing the peg through the perforation such that the frustoconical cap abuts the lower surface of the base pad.

12. The surgical instrument and accessory organizer of claim 11, wherein the at least one retaining member comprises the structure having a pair of resilient arms integrally formed with the disc, the pair of resilient arms projecting from the top surface to receiving at least one tubing.

13. The surgical instrument and accessory organizer of claim 11, wherein the at least one retaining member comprises the structure having a tubing clamp rack having a plate body with an upper surface and a lower surface with slots in the plate body for receiving single tubing clamps, the plate body formed with the disc.

14. The surgical instrument and accessory organizer of claim 11, wherein the at least one retaining member comprises the structure having a hose clamp comprising a ladder-like member comprising flexible and elongate members with at least one rung member there between.

15. A kit comprising:
    a base pad having an upper section and a lower surface and an upper section, the based pad comprising a plurality of perforations extending from the lower surface to the upper surface for removably attaching a plurality of accessories adapted to maintain at least one of an instrument and an object in place;
    a periphery with at least one portion having a longitudinal raised wall with raised walls on either side of the longitudinal raised wall to define a pocket;
    at least one resilient loop integrally formed therewith, the at least one resilient loop having an opening defined therethrough for receiving the at least one of an instrument and an object; a first series of upstanding walls separated from each other by a channel, the channel being dimensioned to receive a shank of the at least one of an instrument and an object and a second series of upstanding walls separated from each other by a slit, the slit disposed collinearly with the first channel to receive a portion of the at least one of an instrument and an object having at least one of a needle point, blade point or other pointed end; and
    at least one retaining member for retaining at least one of the instrument and the object, wherein the at least one retaining member comprises a structure suitable to retain the at least one of the instrument and the accessory, the structure comprising at least one disc integrally formed therewith, the at least one disc having a top surface coupled to the structure and a bottom surface with a peg extending from the bottom surface at one end of the peg and a frustoconical cap at another end of the peg, frustoconical cap comprising a peripheral edge, wherein the frustoconical cap is insertable into the perforations by introducing the peripheral edge into the perforation and pushing the peg through the perforation such that the frustoconical cap abuts the lower surface of the base pad.

16. The kit of claim 15, wherein the at least one retaining member comprises the structure having a pair of resilient arms integrally formed with the disc, the pair of resilient arms projecting from the top surface to receiving at least one tubing.

17. The kit of claim 15, wherein the at least one retaining member comprises the structure having a tubing clamp rack having a plate body with an upper surface and a lower surface with slots in the plate body for receiving single tubing clamps, the plate body formed with the disc.

18. The kit of claim 15, wherein the at least one retaining member comprises the structure having a hose clamp comprising a ladder-like member comprising flexible and elongate members with at least one rung member there between.

\* \* \* \* \*